United States Patent [19]

Branigan

[11] Patent Number: 5,337,744
[45] Date of Patent: Aug. 16, 1994

[54] LOW NOISE FINGER COT PROBE

[75] Inventor: Brendan Branigan, Westlake Village, Calif.

[73] Assignee: Masimo Corporation, Laguna Hills, Calif.

[21] Appl. No.: 91,873

[22] Filed: Jul. 14, 1993

[51] Int. Cl.$^5$ .............................................. A61B 5/02
[52] U.S. Cl. ................................. 128/633; 128/666; 356/41
[58] Field of Search ........................ 128/633, 664–666, 128/880; 356/41

[56] References Cited

U.S. PATENT DOCUMENTS

| | | | |
|---|---|---|---|
| 2,567,926 | 9/1951 | Dunkelberger | 128/880 |
| 4,334,544 | 6/1992 | Hill et al. | 128/666 |
| 4,621,643 | 11/1986 | New, Jr. et al. | 128/633 |
| 4,830,014 | 5/1989 | Goodman et al. | 128/665 |
| 4,867,165 | 9/1989 | Noller et al. | 128/633 |
| 4,907,594 | 3/1990 | Muz | 128/633 |
| 5,031,608 | 7/1991 | Weinstein | 128/880 |
| 5,125,403 | 6/1992 | Culp | 128/633 |

Primary Examiner—William E. Kamm
Assistant Examiner—Robert L. Nasser, Jr.
Attorney, Agent, or Firm—Knobbe, Martens, Olson & Bear

[57] ABSTRACT

A low cost, disposable oximetric sensor including a finger cot probe to facilitate either the transillumination or transreflectance and the detection of optical energy emitted towards a patient's finger without subjecting the finger to deformation. The finger is received within a receptacle having a cup-shaped closed end and an opposite open end that is rolled up upon itself and adapted to be unrolled longitudinally along the finger to form a tubular enclosure in surrounding engagement with the finger. An optical source and an optical detector are arranged in spaced axial alignment with one another at opposite sides of the finger so that optical energy transmitted by the source towards the finger is received by the detector for non-invasively indicating the saturation of oxygen within the patient's blood depending upon the magnitude of the optical energy detected. By virtue of the present invention, decoupling the optical path between the source and detector is minimized in the event that the patient moves his finger during testing.

21 Claims, 5 Drawing Sheets

LOW NOISE FINGER COT PROBE

BACKGROUND OF THE INVENTION

1. Field of the Invention

This invention relates to an inexpensive, disposable oximetric sensor (e.g. a finger cot probe) that is non-adhesively attached to a human digit (e.g. a finger) to facilitate either the transillumination or transreflectance and the detection of electromagnetic (e.g. optical) energy through such digit to analyze the blood of a patient by calculating the concentration of blood constituents (e.g. the saturation of oxygen within the patient's blood) while minimizing potentially interfering noise artifact signals.

2. Background Art

To determine a characteristic within a space, electromagnetic energy is often transmitted through or reflected from a medium to determine its characteristics. In the medical field, instead of extracting material from a patient's body for testing, optical energy can be applied to human tissue so that transmitted or reflected energy can be measured to determine information about the material through which the energy has passed. This form of non-invasive measurement can be performed quickly and easily and has proven to be more comfortable to the patient.

Furthermore, non-invasive physiological monitoring of body functions is often required. For example, during surgery, the available supply of oxygen in the body, or the blood oxygen saturation, is often monitored. This measurement is sometimes performed by non-invasive techniques to enable medical determinations to be made by measuring the ratio of incident to transmitted (or reflected) light through a portion of the body such as, for example, a finger, an ear lobe, or the forehead. Transmission of optical energy as it passes through the body is strongly effected by the thickness of the material through which the energy passes, optical coupling, the optical angle, and the distance between the detector and the source of energy, collectively referred to as the optical path length.

Several parts of the human body are soft and compressible and ideally suited to transmit optical energy. For example, a human digit, such as the finger, comprises skin, muscle, tissue, bone, blood, etc. Although the bone is relatively incompressible, the tissue surrounding the bone is easily compressed when an external pressure is applied to the finger. However, if optical energy is applied to a finger and the patient moves or the finger is compressed in a manner which decouples the optical path between the optical source and detector, the optical path length correspondingly changes. Since a patient moves in an erratic fashion, the compression of the finger and the decoupling of the detector are also erratic. This causes the change in optical path length to be unpredictable and non-compensatable, making the absorption of optical energy erratic, thereby resulting in a noisy, difficult to interpret output signal.

Optical probes have been used in the past for both invasive and non-invasive applications. In the typical optical probe, a light emitting diode (LED) is placed on one side of the human tissue while a photodetector is placed on the opposite side. Such conventional optical probes are primarily useful when a patient is relatively motionless and in environments which are characterized by low ambient room light.

By way of particular example, one well known non-invasive measuring device in which an optical probe is used in health applications is the pulse oximeter which measures pulse rate and the percent of oxygen available in an arterial vessel. Up until the early 1980's, clinicians relied upon arterial blood gas analysis to evaluate gas exchange and oxygen transport within the human body. Although the arterial blood gas test gives valuable information, it only reflects a patient's oxygenation status for one moment in time. On the other hand, pulse oximetry permits a continuous, non-invasive measurement of a patient's arterial oxygen saturation status.

Oxygen saturation is defined as the amount of hemoglobin carried oxygen in relation to its total hemoglobin carrying capacity. Oxygen is carried by hemoglobin cells. A characteristic of hemoglobin is the different ways in which it absorbs both red and infrared light when carrying oxygen in the form of oxyhemoglobin relative to when it is not carrying oxygen in the form of reduced hemoglobin. Pulse oximetry takes advantage of this difference to determine arterial blood oxygen saturation.

An oximetric sensor commonly includes a photodetector and a pair of LEDs which emit both red and infrared light. The sensor is packaged in such a way that the LEDs and photodetector are placed on opposite sides of a vascular bed which, in the transillumination case, is usually a finger, ear lobe or toe. In the reflectance case, the LEDs and the photodetector are placed side by side, but separated by a barrier which blocks light from reaching the detector without first passing through the tissue sample. When properly positioned, the LEDs emit known wavelengths of both red and infrared light for transmission through the vascular bed for receipt by the detector.

As the photodetector receives unabsorbed light which passes through the vascular bed, a signal is produced. This signal is converted to digital form and then supplied to a computer or microprocessor which computes the ratio of red light to infrared light absorption. The absorption data is then utilized to determine the arterial blood oxygen saturation values which may then be displayed on a monitor or a strip chart. Since the light that is directed into the vascular bed is also at least partially absorbed by the nearby tissue and bone material, the oximeter utilizes the alternating bright and dim signals caused by arterial pulsations to further clarify the presence of both reduced hemoglobin and oxyhemoglobin.

By virtue of the foregoing, a health care provider is able to assess second to second changes in a patient's arterial oxygen saturation. This enables the possibility of intervention before hypoxemia occurs. Hypoxemia results from lack of oxygen in the blood which can lead to brain damage or even death. What is more, the health care provider is also able to evaluate the patient's response to treatment on a continuous basis.

Initially utilized in the operating room, pulse oximetry is becoming increasingly common in other parts of the hospital including emergency rooms, adult and neonatal intensive care units, and post anesthesia care units. It is expected that pulse oximeters will also find their way into the general ward and even outside the hospital by medical emergency technicians and private physicians. It is in these new areas that the prior art optical probes (i.e. sensors) have proven to be inadequate due to patient movement and their relatively noisy environment.

One conventional optical sensor that is adhesively attached to a patient's finger is disclosed in U.S. Pat. No. 4,830,014 issued May 16, 1989 to Goodman et al. In its non-applied configuration, this sensor has a plainer I-shape with adhesive covering an entire side. The area of the sensor which is intended to cover the radius of the finger is narrowed so as to provide less stability at the finger tip. This sensor is characterized by a very complex layered structure including a plurality of adhesive backed surfaces laid one atop the other. A first of said adhesive backed surfaces includes apertures through which a light source and optical detector communicate with one another. Another surface firmly engages the patient's finger so as to move therewith. In this sensor configuration, the light source must be precisely aligned with the apertures to insure that light will pass therethrough. As a consequence of the high degree of adhesive attachment between the sensor and the patient's finger, movement of the finger and the corresponding compression of the muscle tissue translates into tension, sudden optical decoupling, and compression of certain surfaces of the sensor.

The foregoing causes a shift in the light path length and a misalignment between the light source and detector. Further compression of the muscle tissue along one side of the finger with tension acting along the other side causes the light source to move relative to the detector along the entire length of the finger. This causes changes to the radiation angles and relocates the detector out of optimum alignment with respect to the light source.

Another known optical sensor is described in U.S. Pat. No. 5,125,403 issued Jun. 30, 1992 to Culp. A woven tube which is folded partially inside itself secures a side-folding light source and detector structure about a patient's finger tip. The finger engages the side-folding structure and pushes it inside the woven tube causing the tube to begin sliding inside out. However, the woven tube is unstable, tending to reverse its inside out movement. Moreover, the side-folding structure can slide off the tip of the finger thereby requiring that the entire assembly be refolded and refitted onto the finger. Flexing the finger can also cause disengagement, and the woven structure does not sufficiently act to straighten the finger after the finger has been flexed.

SUMMARY OF THE INVENTION

In general terms, a low noise, disposable oximetric sensor is disclosed comprising a finger cot probe that is non-adhesively attached to a human digit (e.g. a finger) so that the finger will remain essentially non-deformed during testing. This advantageously avoids the shortcomings associated with conventional optical sensors that are adhesively bonded to a finger and, as described above, are undesirably susceptible to a displacement and a decoupling of the optical source relative to the detector if the patient moves his finger. By virtue of the presently disclosed oximetric sensor, the optical path is preserved and the angular displacement of the detector relative to the sensor is reduced to a minimum.

According to a first embodiment of the finger cot probe, a compact finger cot is disclosed including a rolled proximal end and a cup-shaped distal end. The finger cot is manufactured from a sheer elastic material that is adapted to distribute any occlusive forces evenly along the finger when the probe is applied. The tip of the patient's finger is placed in the cup-shaped distal end of the finger cot, and the rolled proximal end is unrolled longitudinally over the finger. The distal end of the finger cot carries an optical source and an optical detector to be arranged at opposite sides of the patient's finger so that the finger may be transilluminated. The source and detector are recessed within respective cavities formed in the distal end to enable the patient's tissue to enter the cavities when the finger is compressed. By virtue of the foregoing, the optical coupling and path length between the source and detector will remain substantially undisturbed in the event that the patient's finger is moved during testing.

According to a second embodiment of the finger cot probe, a generally planar, flexible protective backing is provided which carries a finger cot at the approximate mid-point thereof. The finger cot is manufactured from a sheer elastic material and includes a rolled proximal end and a cup-shaped distal end. The proximal end is rolled up in a direction so as to lie inside the finger cot. The distal end of the finger cot is connected to the protective backing by means of a pin which extends therebetween. The backing also carries an optical source and an optical detector at opposite ends thereof so as to be spaced from the finger cot. The source and detector are recessed within respective cavities into which the patient's tissue may be received as a result of movement of the finger and the corresponding compression of the patient's tissue. The tip of the patient's finger is placed against the protective backing opposite the cup-shaped distal end of the finger cut, and the rolled proximal end is unrolled over the distal end, whereby the distal end is inverted. The proximal end of the finger cot continues to unroll longitudinally over the finger to force the opposite ends of the flexible protective backing against respective opposite sides of the finger where the optical source and optical detector will be arranged relative to one another to transilluminate the patient's finger.

DETAILED DESCRIPTION

Figure 1:
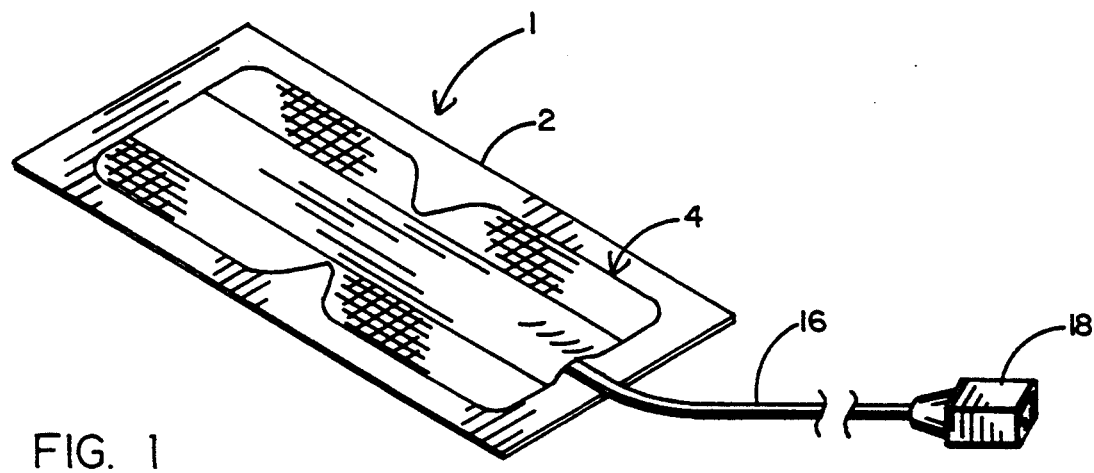
FIGS. 1-3 illustrate a conventional finger cot probe.
Figure 2:
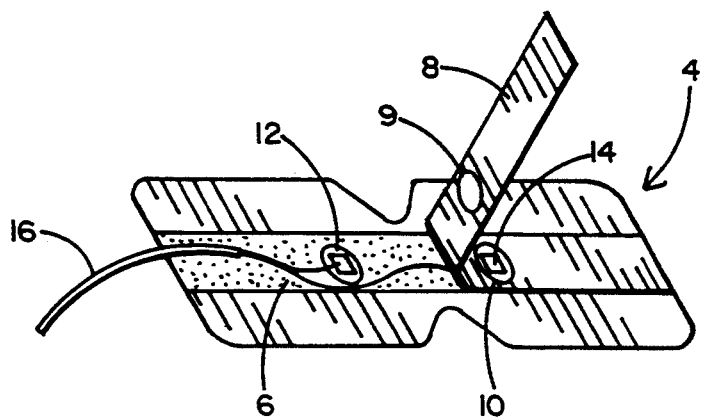
Figure 3:
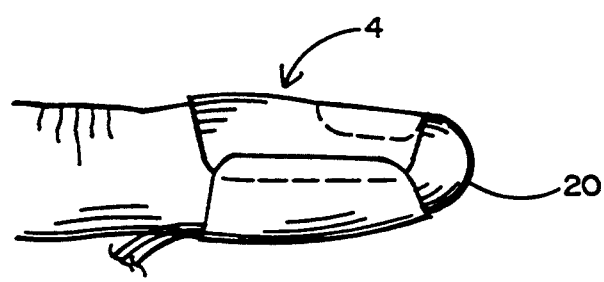
Figure 4:
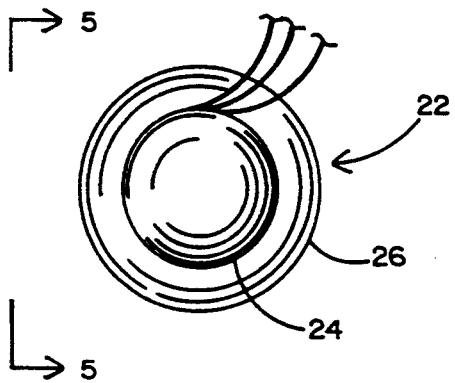
FIG. 4 is a front view of a finger cot probe according to a first embodiment of the present invention.
Figure 5:
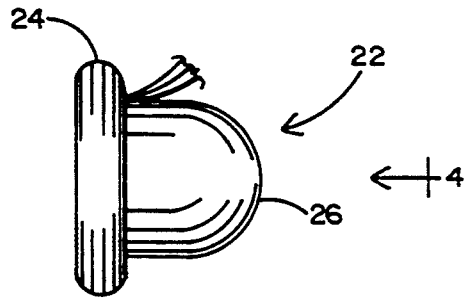
FIG. 5 is a side view of the finger cot probe taken along lines 5-5 of FIG. 4.
Figure 6:
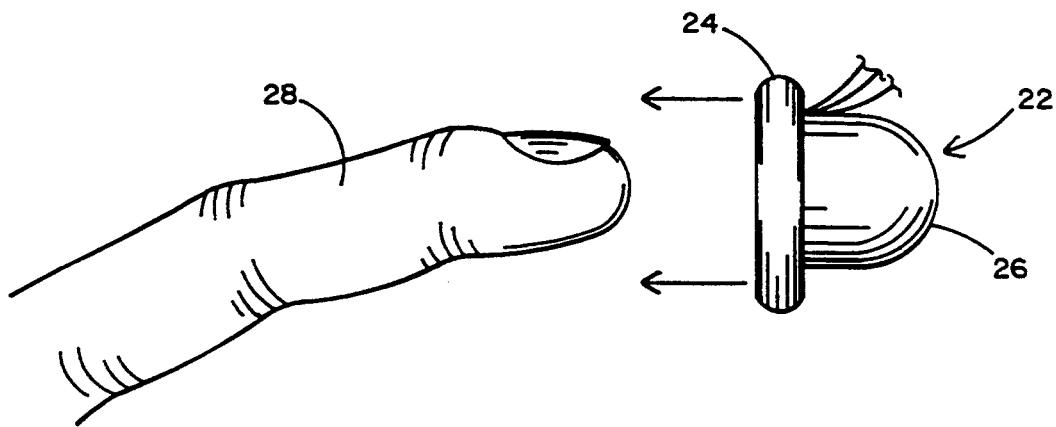
FIGS. 6 and 7 illustrate the steps by which the finger cot probe of the first embodiment is applied to a finger of a patient.
Figure 7:
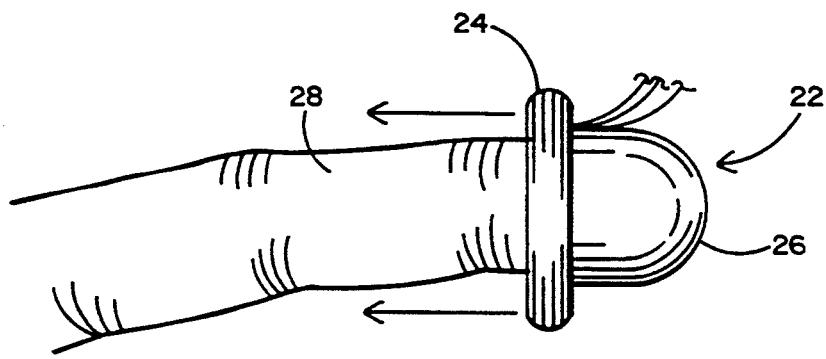

FIGS. 1-3 of the drawings illustrate a known finger cot probe 1 that has been used to provide information concerning blood constituents of a patient. The prior art finger cot probe 1 includes a flat protective backing 2 (best shown in FIG. 1) which carries a removable retaining bandage 4 (best shown in FIG. 2) that is adhesively bonded thereto. Extending longitudinally down the middle of the retaining bandage 4 is a relatively thin adhesive hold down surface 6. A flexible web 8 is retained against the hold down surface 6. The web 8 contains a pair of axially spaced openings 9 and 10 formed therethrough. Each of the openings 9 and 10 is preferably covered by a clear, transparent (e.g. thin plastic) material.

The retaining bandage 4 carries an optical source 12 and an optical detector 14. The optical source 12 is typically a pair of light emitting diodes (LEDs). The optical source 12 and the detector 14 are bonded to bandage 4 at the hold down surface 6 thereof so as to be received within the openings 9 and 10 of web 8 when the web is secured against the hold down surface 6. A wire is attached to each of the LEDs of the optical source 12 and to the optical detector 14. The wires are surrounded by an outer protective casing 16 that terminates at a conventional plug 18. The plug 18 is adapted to be interconnected with a controller (not shown) that supplies and receives signals to and from the optical source and detector 12 and 14.

The face of the retaining bandage 4 is covered with adhesive to permit the bandage to be removably attached to a human finger 20. That is, and as is best shown in FIG. 3, the bandage 4 is tightly wrapped around a patient's finger 20 so that the optical source 12 and optical detector 14 are aligned with one another at opposite sides of the finger 20. In this manner, the optical detector can receive optical signals transmitted through the patient's finger 20 by the LEDs of the optical source 12. After the information is gathered, the retaining bandage 4 is removed from finger 20 and discarded.

Because it is tightly affixed around the patient's finger 20, the adhesively backed retaining bandage 4 is unforgiving in the event that the patient moves his finger during testing. That is to say, and as has been described above, the finger is held in a state of compression, such that any movement during testing tends to decouple the optical source and detector and thereby causes the optical path length to vary. Thus, the signal derived from the finger cot probe of FIGS. 1-3 is often erratic and unreliable.

FIGS. 4-10 of the drawings illustrate one embodiment of the present invention for a disposable, self-adhering finger cot probe that overcomes the unreliability associated with the finger cot probe of FIGS. 1-3. As will soon be explained, the new finger cot probe comprises a compact finger cot 22 that can be quickly and easily attached to and removed from a patient's finger or other digit without the need for or inconvenience associated with a binding and uncomfortable to remove adhesive, such as that common to the conventional finger cot probe of FIGS. 1-3.

In the as-packaged configuration, the finger cot 22 includes an open proximal end 24 that is rolled up upon itself and a closed distal end 26. It is preferable that finger cot 22 be formed from a thin elastic Sheath that is opaque to ambient light. The closed distal end 24 of finger cot 22 is cup-shaped in which to receive the tip of the patient's finger 28. With the finger 28 located at the cup-shaped distal end 26 (best illustrated in FIG. 7), the rolled proximal end 24 is pulled rearwardly and unrolled longitudinally over finger 28, so as to form a generally tubular sleeve by which to surround enough of the finger to form a relatively close fit without generating occlusive pressure which may undesirably lead to tissue thrombosis. That is to say, the elastic sheath will distribute any compressive forces produced by the finger cot 22 evenly along the patient's finger 28. Moreover, the finger cot 22 is quickly and easily attached to finger 28 without the requirement or need for any adhesives or other uncomfortable securing means. Mence, the finger cot 22 may also be easily removed from the finger 28 and discarded at the conclusion of the testing process. The size (e.g. volume) of the finger cot 22 can vary from one probe to another depending upon the age and maturity of the patient.

Figure 8:
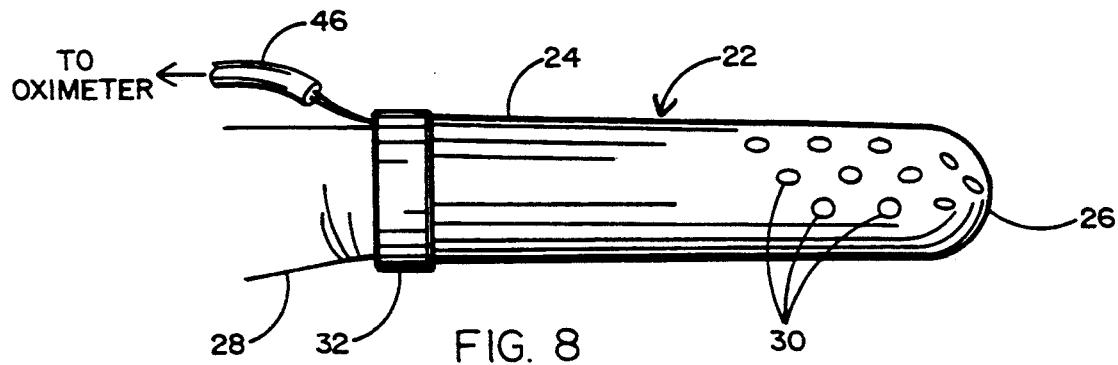
FIGS. 8 and 9 show the finger cot probe fully applied to the patient's finger.

For the purpose of maximizing comfort, a series of optional holes 30 are formed through the sheathing material which forms the finger cot 22 so as to increase air flow to the finger 28 (best illustrated in FIG. 8). When the proximal end 28 is pulled rearwardly so as to be fully unrolled along the patient's finger 28, the finger cot 22 will terminate at a relatively thick peripheral cuff 32 (also best illustrated in FIG. 8) which applies sufficient pressure to enhance the self-attachment of finger cot 22 to the finger 28 without adhesive or other securing means.

Figure 9:
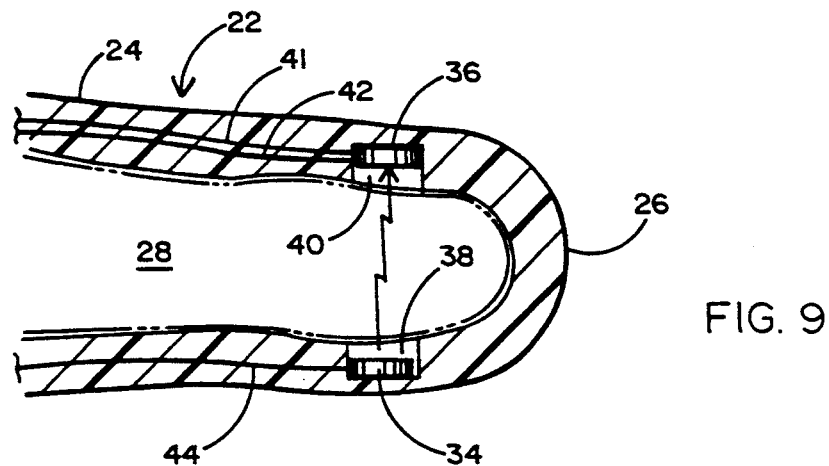

Referring particularly now to FIG. 9, there is shown in the applied, fully unrolled condition of finger cot 22 an optical source 34 and an optical detector 36 arranged in spaced optical alignment with one another at the distal end 26 to transilluminate the patient's finger 28 from opposite sides thereof. By way of example, the optical source 34 is preferably a pair of light emitting diodes (LEDs), only one of which being shown. Both the optical source and detector 34 and 36 are recessed within respective cavities 38 and 40, such that any tissue from the patient's finger 28 which enters the cavities 38 or 40 will be spaced from and out of contact with the optical source and detector 38 and 40. By virtue of the foregoing, the patient's tissue, when compressed, may be received within either cavity 38 and/or cavity 40 without substantial alteration of the optical coupling or path length between the source 34 and detector 36 in the event that the patient's finger is moved during that time when information is gathered. The cavities 38 and 40 may be filled with an optional viscous coupling medium, such as an oil or gel having an index of refraction which corresponds to that of the patient's skin.

A pair of electrically conductive wires 41 and 42 are connected to the LEDs which form optical source 34. Another electrically conductive wire 44 is connected to the optical detector 36. The wires 41, 42 and 44 from the optical source and detector 34 and 36 extend longitudinally through the proximal end 24 of the finger cot 22 to be aligned side-by-side one another and surrounded by an electrically insulating outer protective casing or sleeve 46 (best shown in FIG. 8) as the wires exit the finger cot 22. Outer sleeve 46 carries the wires 41, 42 and 44 to suitable controller and signal processing means (not shown) which will be briefly described hereinafter.

Figure 10:
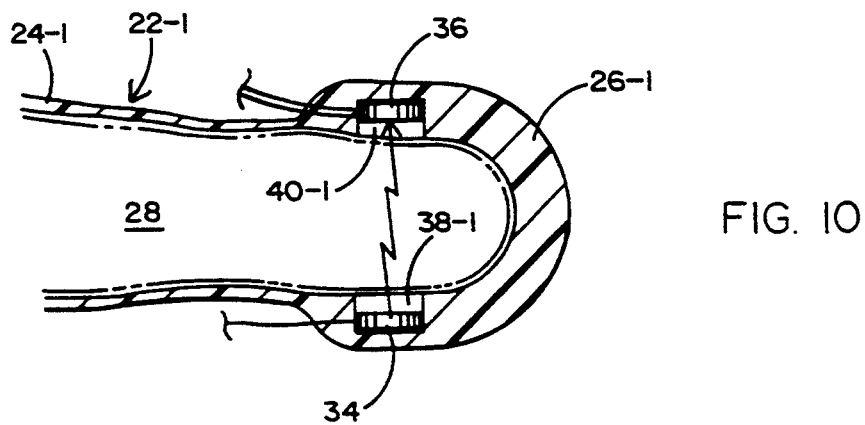
FIG. 10 shows a modified form of the finger cot probe of FIG. 9.
Figure 11:
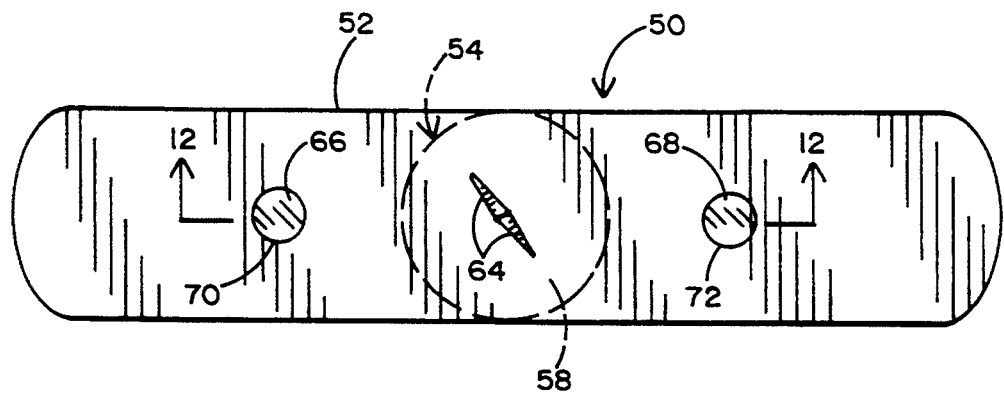
FIG. 11 is a top view of a finger cot probe according to a second embodiment of the present invention.

FIG. 10 of the drawings shows a finger cot 22-1 that is a modified form of the finger cot 22 illustrated in FIGS. 4-9. That is to say, while the proximal and distal ends 24 and 26 of the finger cot 22 are of uniform thickness, the distal end 26-1 of modified finger cot 22-1 is thicker than the proximal end 24-1 thereof. This variation in thickness has been found to make the modified finger cot 22-1 easier to roll into the compact, as-packaged configuration of FIGS. 4 and 5.

FIGS. 11-15 of the drawings show a finger cot probe 50 according to a second embodiment of the present invention. The probe 50 includes a generally planar protective backing or carrier 52 which is preferably formed from a flexible (e.g. plastic) material. Carried at the approximate midpoint of the protective backing 52 of probe 50 is a finger cot 54 manufactured from a thin, elastic sheath that is opaque to ambient light. Like the finger cot 22 described when referring earlier to FIGS. 4 and 5, the finger cot 54, in the as-packaged configuration, includes an open proximal end 56 that is rolled up upon itself and a closed, cupshaped distal end 58. However, the proximal end 56 is rolled up so as to lie inside the finger cot 54 (represented by phantom lines in FIGS. 12 and 13).

The finger cot 54 is attached to the protective backing 52 by means of a pin 60. The pin 60 has a narrow body, a relatively wide pin head 62 at one end of the body and a pair of flexible legs or ties 64 at the opposite end. The pin 60 extends through both the protective backing 52 of finger cot probe 50 and the distal end 58 of finger cot 54, such that the pin head 62 connects the finger cot 54 at one side of the backing 52 with the flexible legs 64 projecting outwardly from the opposite side. The legs 64 are bent downwardly towards and secured (e.g. sewn) to the backing 52 for reliably securing the finger cot 54 to the backing. In this position, the legs 64 provide the advantage of a target towards which the patient's finger is aimed when the finger cot 54 is applied (best shown in FIG. 13).

While the optical source 34 and detector 36 of the finger cot probe of FIGS. 4–10 were included as an integral part of the finger cot 22, the finger cot probe 50 of the present embodiment includes an optical source 66 and an optical detector 68 (e.g. a pair of LEDs) which are separated from the finger cot 54. More particularly, the optical source and detector 66 and 68 are retained at opposite ends of the protective backing 52 of probe 50 and spaced from the finger cot 54. The optical source and detector 66 and 68 are recessed within respective cavities 70 and 72 so that the patient's tissue may be received therein without contacting either the source or detector to preserve the optical coupling and path length therebetween in the event that the patient's finger is moved and the tissue compressed during testing.

Figure 12:
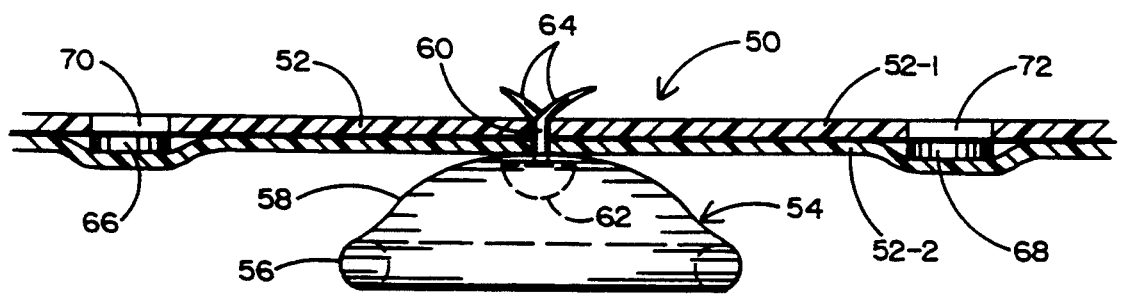
FIG. 12 is a cross-section taken along lines 12-12 of FIG. 11.

To facilitate the formation of the cavities 70 and 72, the protective backing 52 of probe 50 may be formed by top and bottom layers 52-1 and 52-2 of flexible material (best shown in FIG. 12). The optical source and detector 66 and 68 are carried by the bottom layer 52-2 while the cavities 70 and 72 are formed through the top layer 52-1 in axial alignment with the source and detector. Moreover, the electrically conductive wires (best shown in FIG. 15) that are connected from the source and detector 66 and 68 to controller and signal processing means (not shown) may extend through the finger cot probe 50 at the interface between the top and bottom layers 52-1 and 52-2 of protective backing 52. In this regard, an electrically insulating outer protective casing or sleeve 78 (also best shown in FIG. 15) surrounds the wires as they exit the probe 50.

Figure 13:
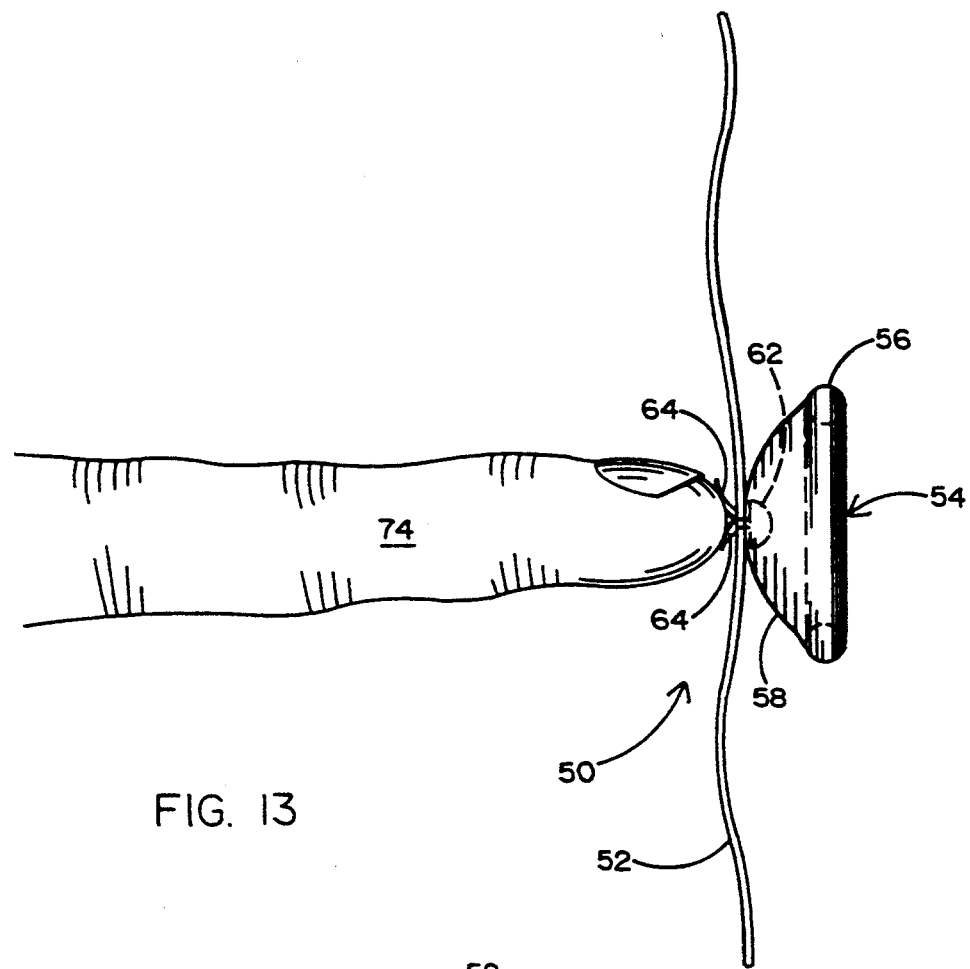
FIGS. 13 and 14 illustrate the steps by which the finger cot probe of the second embodiment is applied to a finger of a patient.
Figure 14:
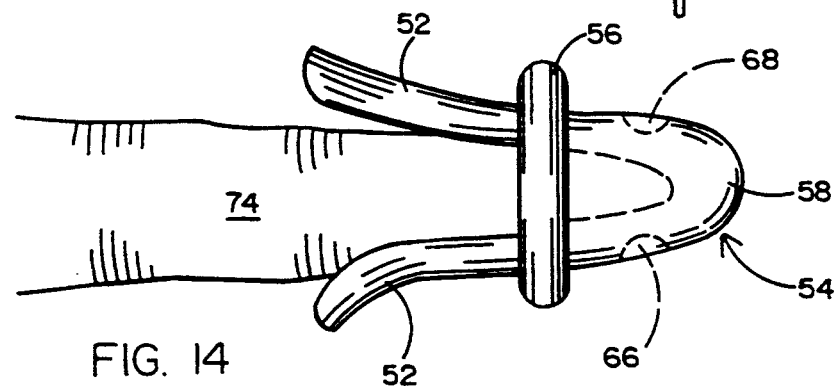
Figure 15:
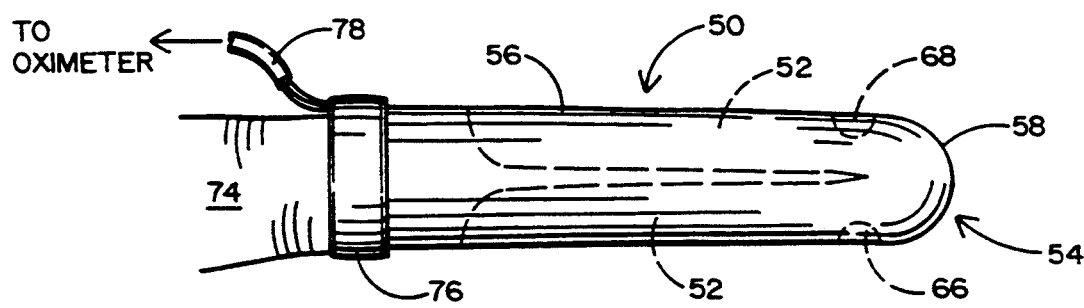
FIG. 15 shows the finger cot probe fully applied to the patient's finger.

FIGS. 13–15 illustrate the steps for applying the finger cot probe 50 to a patient's finger 74 from the as-packaged rolled configuration of the finger cot 54 (best shown in FIG. 13) to the fully unrolled configuration (best shown in FIG. 15). The patient's finger 74 is first placed on the target formed at the intersection of the flexible legs 64 of the pin 60 opposite the unrolled distal end of finger cot 54. To this end, a small amount of adhesive may be applied to the legs 64 merely to hold the finger 74 against the target during application of the finger cot 54. The unrolled proximal end 56 of finger cot 54 is then pulled rearwardly towards finger 74 and unrolled over the cup-shaped distal end 58 of the finger cot, whereby the distal end is inverted and the patient's finger is surrounded thereby. The continued rearward movement of the proximal end 56 over the protective backing 52 so as to form a generally tubular sleeve also forces the opposite ends of the backing towards one another and against respective opposite sides of the finger 74.

In the fully unrolled and applied condition of the finger cot probe 50, the protective backing 52 is bent and retained around the finger 74, such that the optical source and optical detector 66 and 68 are held in spaced optical alignment with one another at opposite sides of the finger 74 so that the finger may be transilluminated. The fully unrolled finger cot 54 terminates at a relatively thick peripheral cuff 76 (best shown in FIG. 15) which applies sufficient pressure to attach the finger cot 54 to the finger 74 without hard to remove or uncomfortable adhesive or other retaining means.

The optical detectors described with regard to the finger cot probes 22 and 50 which form this invention are responsive to light absorption from the transillumination of the patient's muscle tissue. More particularly, the output signals provided by the detector can be digitally encoded and then processed for the purpose of enabling health care providers to analyze the patient's blood by non-invasively calculating the concentration of blood constituents. For example, the output signals derived from the optical detectors can be used to provide a reliable indication of the saturation of oxygen within the patient's blood. The foregoing may be accomplished by means of a pulse oximeter which receives from the optical detector two output signals having different wavelengths, one of which is typically red and the other of which is typically infrared. The two signals are alternately passed through the patient's finger by the optical source. The signals are measured at the optical detector and are then processed to determine the amount of oxygen available to the body. This information is evaluated to derive the saturation of oxygenated hemoglobin in the blood comprising both oxygenated and deoxygenated hemoglobin.

One pulse oximeter which is especially suitable for use herein with finger cot probes 22 and 50 is that described in co-pending U.S. patent application Ser. No. 672,890 filed Mar. 21, 1991 and assigned to the assignee of this patent application. Therefore, the teachings of patent application Ser. No. 672,890 relating to pulse oximetry are incorporated herein by reference. However, it is to be understood that this oximeter is given for purposes of example only, and the particular pulse oximeter selected for processing the output signals from the optical detectors forms no part of the claimed invention.

It will be apparent that while a preferred embodiment of the invention has been shown and described, various modifications and changes may be made without departing from the true spirit and scope of the invention. For example, although the finger cot probes herein have been described as having particular use with a patient's finger, it is to be expressly understood that the teachings of this invention are also applicable to any other human digit or suitable palpable tissue area. What is more, while the optical detectors herein have been described as being responsive to the transillumination of human tissue, it is also to be understood that the optical detectors may be suitably located to be responsive to transreflectance, as well.

Having thus set forth the preferred embodiment of this invention, what is claimed is:

1. A sensor for analyzing human tissue, said sensor having a body and comprising:
   a first end of said body at which to receive some of the tissue to be analyzed;
   a flexible opposite end of said body rolled up upon itself in a direction towards and spaced a first distance from said first end, said opposite end moved in a direction away from said first end to unroll said opposite end so as to surround said tissue, the unrolled end being spaced a substantially greater distance from said first end than the first distance between said rolled end and said first end;
   electromagnetic energy source means carried by said first end to emit electromagnetic energy towards the tissue to be analyzed; and
   electromagnetic energy detector means carried by said first end and arranged relative to said source means to receive the electromagnetic energy emitted by said source means, the magnitude of the electromagnetic energy received by said detector means providing information regarding said tissue.

2. The sensor recited in claim 1, wherein the first end of said sensor is cup-shaped to receive the tissue to be analyzed therewithin.

3. The sensor recited in claim 2, wherein said cup-shaped first end is coextensively connected to said rolled up opposite end, said opposite end being unrolled away from said first end to form a generally tubular configuration in surrounding engagement with said tissue.

4. The sensor recited in claim 1, further comprising holes formed through said first end to provide ventilation for the tissue received thereat for analysis.

5. The sensor recited in claim 1, wherein said electromagnetic energy source means is an optical source and said electromagnetic energy detector means is an optical detector.

6. The sensor recited in claim 5, wherein said optical source includes a pair of light emitting diodes that emit optical signals with respective wavelengths in the red and infrared ranges.

7. The sensor recited in claim 5, further comprising first and second cavities formed in said first end thereof, said optical source and said optical detector being received within respective ones of said cavities.

8. The sensor recited in claim 7, wherein said optical source and said optical detector are recessed within said respective cavities so as to avoid contact with any tissue to be analyzed that enters said cavities.

9. The sensor recited in claim 7, wherein said first and second cavities are arranged in spaced axial alignment with one another at opposite sides of said first end so that the tissue at said first end is transilluminated by optical signals emitted from said optical source.

10. The sensor recited in claim 1, wherein said opposite end thereof includes an elastic cuff to surround said tissue and thereby hold said sensor in engagement therewith when said opposite end is unrolled away from said first end.

11. The sensor recited in claim 1, wherein said first end thereof is thicker than said opposite end.

12. The sensor recited in claim 1, wherein said first and opposite ends thereof form a finger cot to receive and surround a human finger to analyze the blood circulating through the finger.

13. Apparatus for analyzing human tissue, said apparatus comprising:
   flexible carrier means for engaging the human tissue to be analyzed at one side of said carrier means, said carrier means including electromagnetic energy source means to emit electromagnetic energy towards said tissue and electromagnetic energy detector means to detect the energy emitted by said electromagnetic energy source means; and
   tissue receptacle means having a first end attached at a side of said carrier means opposite the one side thereof engaging said tissue and a flexible opposite end rolled up upon itself and adapted to be unrolled over said first end in a direction towards said carrier means so as to surround the tissue to be analyzed and simultaneously move said carrier means around said tissue such that said detector means is arranged relative to said source means to receive the electromagnetic energy emitted by said source means,
   the magnitude of the electromagnetic energy received by said detector means providing information regarding said tissue.

14. The apparatus recited in claim 13, wherein the first end of said tissue receptacle means is cup-shaped curving away from said carrier means, said cup-shaped first end being inverted and thereby curving towards said carrier means to surround the tissue to be analyzed when the opposite rolled up end of said receptacle means is unrolled over said first end towards said carrier means.

15. The apparatus recited in claim 14, wherein the cup-shaped first end of said tissue receptacle means is coextensively connected to said rolled up opposite end thereof, said opposite end being unrolled over said first end to form a generally tubular configuration in surrounding engagement with said tissue to be analyzed, said carrier means being moved between said unrolled opposite end and said tissue.

16. The apparatus recited in claim 13, wherein said electromagnetic energy source means is an optical source and said electromagnetic energy detector means is an optical detector.

17. The apparatus recited in claim 16, wherein said carrier means also includes first and second cavities, said optical source and said optical detector received within respective ones of said cavities.

18. The apparatus recited in claim 17, wherein said optical source and said optical detector are recessed within said respective cavities so as to avoid contact with any tissue to be analyzed that enters said cavities.

19. The apparatus recited in claim 17, wherein said carrier means is planar, said first and second cavities located at opposite ends of said planar carrier means and arranged in spaced alignment with one another at opposite sides of the tissue to be analyzed when said carrier means is moved around said tissue so that said tissue is transilluminated by optical signals emitted from said optical source.

20. The apparatus recited in claim 13, wherein said carrier means and said tissue receptacle means form a finger cot probe, said receptacle means for surrounding a human finger to analyze the blood circulating through said finger.

21. A method for analyzing human tissue by means of a tissue receptacle having a first closed end and an opposite open end that is rolled up upon itself such that said first closed end and said opposite rolled up end are spaced a first distance from one another, said method comprising the steps of:

unrolling the rolled up open end of said receptacle away from said final end so as to form a tubular enclosure with said closed first end for surrounding said tissue, the length of said tubular enclosure between said unrolled open end and said closed first end being substantially greater than the first distance between said rolled up open end and said closed end;

locating a source of electromagnetic energy at one side of said tissue to be analyzed to transmit electromagnetic energy towards said tissue;

locating a detector of electromagnetic energy at the opposite side of the tissue to be analyzed to receive the electromagnetic energy transmitted by said source; and computing the magnitude of the electromagnetic energy received by said detector from said source for providing information regarding said tissue.

* * * * *